(12) United States Patent
Kruse et al.

(10) Patent No.: US 8,735,151 B2
(45) Date of Patent: May 27, 2014

(54) SPONTANEOUSLY CONTRACTING FISH CELL AGGREGATES, USE THEREOF AND METHOD FOR THE PRODUCTION THEREOF

(75) Inventors: Charli Kruse, Herrnburg (DE); Bianka Grunow, Luebeck (DE); Daniel Hans Rapoport, Luebeck (DE); Philipp Ciba, Luebeck (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 37 days.

(21) Appl. No.: 13/394,586

(22) PCT Filed: Sep. 8, 2010

(86) PCT No.: PCT/EP2010/005509
§ 371 (c)(1),
(2), (4) Date: Mar. 7, 2012

(87) PCT Pub. No.: WO2011/029584
PCT Pub. Date: Mar. 17, 2011

(65) Prior Publication Data
US 2012/0171695 A1 Jul. 5, 2012

(30) Foreign Application Priority Data
Sep. 11, 2009 (DE) .......................... 10 2009 041 254

(51) Int. Cl.
*C12N 5/00* (2006.01)

(52) U.S. Cl.
USPC .......................................... 435/325; 435/378

(58) Field of Classification Search
USPC ................................................ 435/325, 378
See application file for complete search history.

(56) References Cited

FOREIGN PATENT DOCUMENTS

WO    2005108598 A1    11/2005

OTHER PUBLICATIONS

Hyodo et al. (A novel in vitro system for studying cardiomyoctye differentiation with medaka embryonic cells. (2009) Int. J. Dev. Bio. 53: 615-622).*
Grunow et al. (In vitro expansion of autonomously contracting cardiomyogenic structures from rainbow trout *Oncorhynchus mykiss*. Journal of Fish Biology. Feb. 2010 76(2):427-424).*
Brette et al., "Characterization of isolated ventricular myocytes from adult zebrafish (*Danio rerio*)", Biochemical and Biophysical Research Communications, vol. 374, pp. 143-146 (2008).
Driever et al., "Characterization of a Cell Line Derived from Zebrafish (*Brachydanio rerio*) Embryos", In Vitro Cell Dev. Biol., vol. 29A, pp. 749-754 (1993).
Fraunhofer EMB, "Project Example: Preparation of autonomously contracting cell aggregates from cells of the rainbow trout", Jahresbericht (2008), p. 51.
Goldstein et al., "Are primary cultures of trout (*Oncorhynchus mykiss*) ventricular cardiomyocytes metabolically viable?", Fish Physiology and Biochemistry, vol. 30, pp. 109-117 (2004).
Grunow et al., "In vitro expansion of autonomously contracting, cardiomyogenic structures from rainbow trout *Oncorhynchus mykiss*", Journal of Fish Biology, vol. 76, pp. 427-434 (2010).
Kimmel et al., "Stages of Embryonic Development of the Zebrafish", Developmental Dynamics, vol. 203, pp. 253-310 (1995).
Kumar et al., "Efficacy of fish and prawn muscle extracts as supplements of medium in development of a primary cell culture system from larval tissue of aquarium fish *Poecilia reticulata*", Indian Journal of Experimental Biology, vol. 36, pp. 91-94 (1998).
Nurmi et al., "Electrophysiological properties of rainbow trout cardiac myocytes in serum-free primary culture", Am. J. Physical Regulatory Integrative Comp Physiol, vol. 282, pp. R1200-R1209 (2002).
Singh et al., "Development of primary cell cultures from kidney of fresh water fish *Heteropneustus follilis*", Indian Journal of Experimental Biology, vol. 33, pp. 595-599 (1995).
Tytgat, "How to isolate cardiac myocytes", Cardiovascular Research, vol. 28, No. 2, pp. 280-283 (1994).
International Search Report for PCT/EP2010/005509 dated Dec. 16, 2010.
Written Opinion of the International Searching Authority relating to PCT/EP2010/005509, 2010.

* cited by examiner

*Primary Examiner* — Karen Cochrane Carlson
*Assistant Examiner* — Natalie Moss
(74) *Attorney, Agent, or Firm* — Caesar, Rivise, Bernstein, Cohen & Pokotilow, Ltd.

(57) ABSTRACT

The invention relates to an in vitro method for producing spontaneously contracting fish cell aggregates, to the fish cell aggregates obtained thereby, and to the use thereof, in particular for testing biological active substances and pharmaceuticals. The in vitro method according to the invention for producing contracting fish cell aggregates comprises the following steps: a) mechanical comminution and/or partial enzymatic digestion of fish embryos or fish larvae; b) transfer of the comminuted and/or partially digested fish tissue into an enzyme-free medium and removing the supernatant by centrifuging to obtain a cell pellet; c) re-suspension of the cell pellet in a cell culture medium; d) culturing the cells, with the medium being changed at least once, until spontaneously contracting cell aggregates form.

11 Claims, 9 Drawing Sheets
(7 of 9 Drawing Sheet(s) Filed in Color)

| Antibodies | Cryosection of heart of an adult rainbow trout | Beating cell aggregates |
|---|---|---|
| Anti-Troponin I antibody (dil.: 1:50; Acris, Germany) |  |  |
| Anti-alpha-actinin antibody (dil.: 1:50; Sigma Aldrich, Germany) |  |  |
| Anti-N-cadherin antibody (dil.: 1:50; BD Biosciences, Germany) |  |  |
| Anti-beta-catenin antibody (dil.: 1:10; BD Biosciences, Germany) |  |  |
| Anti-desmoplakin antibody (dil.: pure; PROGEN, Germany) |  |  |

|       | SCC1 | SCC2 | SCC3 | PK | VK |        |
|-------|------|------|------|----|----|--------|
| elfa  |      |      |      |    |    | 272 bp |
| α-actin |    |      |      |    |    | 102 bp |
| myh6  |      |      |      |    |    | 211 bp |
| cx43  |      |      |      |    |    | 161 bp |

Fig. 7

December 2009

Fig. 8A

January 2010

SPONTANEOUSLY CONTRACTING FISH CELL AGGREGATES, USE THEREOF AND METHOD FOR THE PRODUCTION THEREOF

BACKGROUND OF THE INVENTION

The invention relates to an in vitro method for producing spontaneously contracting fish cell aggregates, to the fish cell aggregates obtained thereby, and to the use thereof, in particular for testing biological active substances and pharmaceuticals.

Cardiovascular diseases are one of the most common causes of death, and a more successful treatment and prevention of these diseases is the objective of substantial investments and research efforts. Besides improved implantation and transplantation methods, also by using new synthetic or semi-synthetic organs or organ components, such as blood vessels, bypasses, heart valves, etc., the primary approach is the development of new pharmaceuticals which have a direct or indirect effect on the cardiac activity and specifically influence the heart muscle cells or other heart cells, for example. Traditionally, animal experiments are conducted to test such active substances.

However, both for ethical and cost reasons, the aim is to keep the number of animal experiments in pharmaceutical tests as low as possible and to perform at least the first test stage in vitro with cells or cell cultures.

To this end, for example, cell cultures of adult human cardiac cells, in particular cardiomyocytes, or of corresponding cells from other mammal species, e.g. pigs, hitherto had to be used. However, these cells typically cannot be cultivated or do not behave like cells in a natural tissue (e.g., they do not form any contracting or contractible cell aggregates or dedifferentiate in the cell culture). Other non-human cells are different from the human cells with regard to their behavior and their properties. Cardiomyocytes from mice or rats for example have ion channels which differ from those of the corresponding human cells.

In light of this, the object of the invention is the provision of improved cell cultures and in vitro systems for testing biological active substances and pharmaceuticals which in general have an effect on the cardiac activity and specifically have an effect on heart muscle cells or other heart cells wherein the cell cultures and test systems should reflect the behavior and properties of human heart cells in a natural tissue better than previous in vitro systems and even many animal models.

This object is solved by the method for producing the spontaneously contracting cell aggregates according to the invention, the material compositions and cell cultures containing these spontaneously contracting cell aggregates according to the invention and the use of these cell aggregates according to the invention.

DESCRIPTION OF THE INVENTION

The in vitro method according to the invention for producing spontaneously contracting fish cell aggregates according to claim 1 comprises the following steps:
a) mechanical comminution and/or partial enzymatic digestion of fish embryos or fish larvae;
b) transfer of the comminuted and/or partially digested fish tissue into an enzyme-free medium and removing the supernatant by centrifuging to obtain a cell pellet;
c) resuspension of the cell pellet in a cell culture medium;
d) cultivation of the cells, with the medium being changed at least once, until spontaneously contracting cell aggregates form.

Any fish species is in principle suitable as a source for the fish embryos or fish larvae used according to the invention, preferably those from Osteichthyes, in particular the species of Teleostei. Specific examples thereof are the species of herrings (Clupeoidei), salmon-like fish (Salmonoidei), carps (Cyprimidae), eels (Anguillidae), perches (Percidae), cods (Gadidae), catfish (Siluroidae), flatfish (Pleuronectiformes), garfish (Beloniformes), sturgeons (Acipenseriformes), etc.

The species of salmon-like fish, e.g. salmons, trouts, in particular brown trouts, rainbow trouts, samlets, huchens, whitefish, graylings, smelts, are particularly preferred.

The term "fish embryos" or "fish larvae", as used herein, comprises in particular fish eggs or fish larvae from the eyed egg stage (formation of eyed eggs) to the end of the yolk sac stage (feeding on the yolk sac).

For the method according to the invention, the partial enzymatic digestion may be any proteolytic digestion known in the prior art for the digestion of animal tissue (e.g. using collagenase, chymotrypsin or other proteinases) and comprises or typically consists of trypsin treatment, in particular trypsin-EDTA treatment.

The conditions of the enzymatic treatment are chosen such that in any case, intact unions of cells still exist after the treatment and not only a pure single-cell suspension is present.

The optimum conditions for the respective type can be determined by the person skilled in the art by routine experimentation. Typically, the enzyme treatment, e.g. trypsin-EDTA treatment, is performed in a buffer with 0.01-1% enzyme, e.g. trypsin, for a period of 15 seconds to 10 minutes, preferably 30 seconds to 2 minutes.

In the case of a trypsin treatment, it is particularly advantageous (but not essential) to establish the conditions such that:
- the volume of the sterile trypsin solution corresponds to about double to triple the tissue volume;
- the tissue pieces are uniformly mixed with the solution;
- the digestion is carried out with 37° C. warm trypsin solution at 37° C.;
- the preparations are repeatedly admixed during the digestion;
- the comminution of the tissue at the end of the digestion is enhanced by pipetting;
- the samples are quickly cooled down to their incubation temperature (4-25° C.) at the end of the digestion by means of briefly placing them on ice.

Besides the enzymatic treatment, a coarse mechanical comminution, e.g. by means of scissors, is preferably carried out whereby tissue pieces in a size range of typically about 0.05-5 mm, for example 0.05-3 mm or 1-5 mm, are produced. However, a more intense comminution is possible without causing damage, and it is even possible to dispense with the enzymatic treatment completely and effect the tissue digestion exclusively by an intense mechanical comminution.

To end the enzymatic treatment, the comminuted tissue is transferred into an enzyme-free medium and the supernatant is removed by centrifugation. The centrifugation is carried out with a low g value and its sole purpose is to separate a cell pellet from the liquid supernatant. The centrifugation is typically performed at 100 to 180 g.

The cultivation is carried out in a customary cell culture medium, e.g. DMEM with FBS, at temperatures optimized for the respective fish cells, typically in a range of from 4 to 28° C., for example 4 to 25° C., preferably 15 to 22° C. The cultivation is preferably carried out in the presence of $CO_2$, e.g. 0.5 to 10% $CO_2$, preferably 1 to 5% $CO_2$.

After several days of cultivation, typically 3 to 7 days, areas with spontaneously contracting cell aggregates can be seen under a microscope.

The easy cultivation of the fish heart cells and the spontaneous formation of contracting cell aggregates represent an immense advantage in comparison to the mammalian cell cultures of the prior art.

The term "spontaneously contracting cell aggregates", as used herein, means that contractions (and expansions) of the cell aggregates take place without any external stimulation, e.g. by an applied voltage. "Spontaneously contracting" cell aggregates are herein also referred to as "beating" or "twitching" cell aggregates.

The cell aggregates and cell cultures produced with the method according to the invention can be subjected to several passages (for example at least 1 passage). In the course of this, the ability of the aggregates to spontaneously contract is basically retained, but the regularity and/or contraction frequency ("beating frequency") can be changed temporarily or permanently (see characterization experiments in the examples). This effect could be used to obtain particularly advantageous contraction properties of the cell aggregates. The shape of the cell aggregates is also variable but in each case defined; for example, spherical and tubular cell aggregates were observed (FIG. 3).

Another aspect of the invention relates to the fish cell aggregates themselves which can be produced with the above-described method according to the invention and have the ability to spontaneously contract as well as material compositions and cell cultures containing these cell aggregates.

In contrast to natural contractible cell aggregates in fish, the contracting fish cell aggregates according to the invention are not part of an organism or a tissue formed in an organism.

The mentioned material compositions can further comprise a carrier or envelope material. The carrier material can form a three-dimensional matrix, for example, and consist of natural or synthetic polymers.

In vitro systems including these cell aggregates or material compositions offer advantageous application possibilities in diverse areas of research.

Developmental biology: studies on the development of a heart with an examination of diverse channels, proteins, etc.

Pathology: application of cause-and-effect complexes to the field of fish pathology. Each year, millions of fish die from the cardiomyopathy syndrome (CMS), for example. Hitherto, it was only possible in this field to carry out research on organisms. The systems according to the invention would also allow for research on a cell level.

Regenerative medicine: Thanks to the high regeneration, for the first time, the regeneration of fish heart cells can also be examined on a cell level which hitherto was only possible with live fish (zebrafish).

Examinations of the inventors have proven that aggregates derived from two different fish larvae can coalesce and the contraction is adjusted. It was shown that a functioning syncytium can be produced from originally two aggregates by means of cell connection proteins. The use of such aggregates would be of interest of both research and regenerative medicine as the aggregation of tissues foreign to the cell could be examined on the level of unions of cells. This subject matter is of great importance in the examination of rejection reactions in transplantations, for example.

Pharmacology: As the heart cell aggregates can be generated in high numbers, the in vitro system can be used as a high-throughput test system. Another advantage is their spontaneous contraction. In most cases, previous models had to be electrically stimulated which can lead to false results. Long-term testing is also possible thanks to a very long stability at the aggregates. Furthermore, mouse cells are hitherto primarily used in pharmacology for testing human drugs. As the electrophysiological properties of the murine cardiomyocytes differ significantly from human cardiomyocytes, very often different reactions to drugs result. In contrast, the fish aggregates show very strong similarities to human cardiomyocytes such that the same ion channels occur as in humans. As the system according to the invention is also three-dimensional, drugs could be tested in pharmacology for the first time on spontaneously contracting 3D unions of cells.

An important particular application of these material compositions or cell cultures relates to their use for testing biological active substances (including cosmetics) or pharmaceuticals.

Figure 10A:
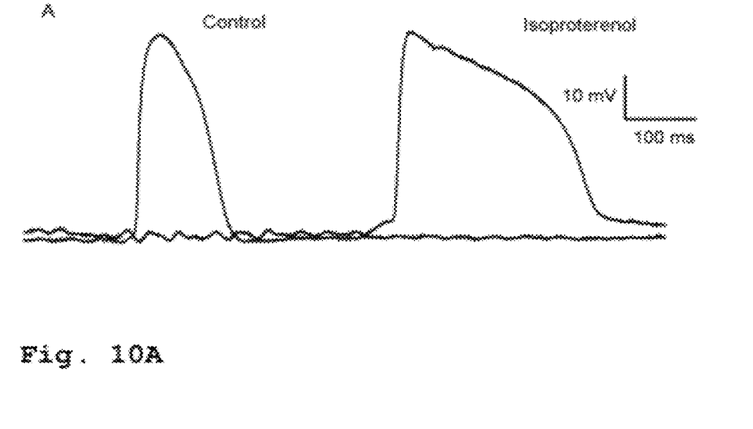
FIG. 10 Effect of cardiac drugs on the cell aggregates; A: isoproterenol (calcium channel agonist); B: rilmakalim (potassium channel blocker)
Figure 10B:
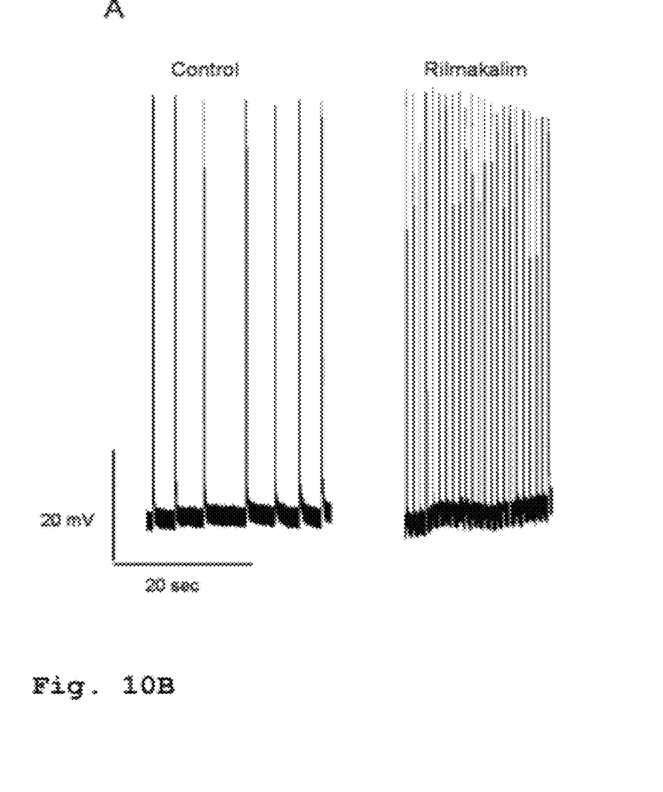

In doing so, biological active substances or pharmaceuticals are preferably tested with regard to their effect on heart muscle cells or other heart cells. Exemplary drug tests are described in example 5 and FIG. 10.

The material compositions and cell cultures with spontaneously contracting cell aggregates provided according to the invention are particularly well suited for this application as they can be easily produced, even in large amounts, and have many properties which are surprisingly very similar to those of human cells, more similar than e.g. mammalian cells such as from mice, rats or pigs. This applies in particular to the cardiomyocytes which form the main component of the contractible fish cell aggregates, when compared to human cardiomyocytes (see also Brette et al. Biochem. (2008) Biophys. Res. Commun. 374, 143-146). Thus, according to the invention a simple, but effective in vitro model system for human cardiomyocytes or heart (muscle) tissue for testing biological active substances or pharmaceuticals with regard to their effect on heart muscle cells or other heart cells can be provided by means of these fish cell aggregates.

Extensive examinations by the inventors have shown that the generated cell aggregates from larvae of different ages present markedly different contractions. The contractions were determined for each aggregate over a period of three weeks by means of optical microscopy and video recordings. The age of the larvae is given in day degrees as, additional to the type of fish, the development time of fish eggs/embryos and fish larvae strongly depends on the water temperature. If the water is warmer, the larvae hatch quicker. Therefore, temperature and days are multiplied with each other for the unit of measure "day degrees".

In principle, the generation of spontaneously contracting aggregates is possible from the beginning of the "eyed egg stage" (210 day degrees) to the end of the "yolk sac stage" (500 day degrees). In particular with regard to the conformity with human heart cells or heart cell aggregates, however, a marked optimum exists in a particular development stage shortly before and after the hatching of the fish larvae, in particular up to about 1-50 day degrees before or after. For rainbow trouts, this stadium is in the range of from about 320 to 400 day degrees.

As can be seen from the following tables, among the test aggregates, the aggregates of the preparation of 378 day degrees (shortly after hatching) has the best conformity and the slightest deviations from the human contraction frequency. The electrophysiological examinations also showed that the resting membrane potential for hatched larvae is closer to that of humans (at −60 mV) than for aggregates of larvae in the egg (<−50 mV).

| Larvae age in day degrees | Development stage | Generation ratio | Contraction frequency |
|---|---|---|---|
| 250 | Egg | 0.4 | 30 |
| 295 | Egg | 0.6 | 70 |
| 335 | Egg | 1.5 | 70 |
| 378 | Yolk sac | 0.6 | 90 |
| 420 | Yolk sac | 0.8 | 70 |
| 462 | Yolk sac | 0.5 | 70 |

| Larvae age in day degrees | Median value of contraction frequency | Minimum value of contraction frequency | Maximum value of contraction frequency |
|---|---|---|---|
| 252 | 25 | 22 | 37 |
| 294 | 65 | 42 | 75 |
| 335 | 60 | 30 | 83 |
| 378 | 90 | 85 | 92 |
| 420 | 62 | 45 | 81 |
| 426 | 70 | 43 | 90 |

The ratio (yield of aggregates) at 378 day degrees can be optimized as the previous and subsequent ratios were higher such that a different treatment of the larvae can be assumed in this case. Thus, the formation of aggregates can be increased by shortening the anesthetic incubation.

The use of freshly hatched larvae further offers the advantage of an easier manipulation in comparison to isolation from the egg as the larva no longer has to be isolated from the egg. Furthermore, the aggregates are bigger with increasing larvae age such that electrophysiological examinations can be carried out more easily.

It could be shown that the aggregates obtained according to the invention are stable for a period of several weeks (up to 2 months) with regard to their contraction and thus are significantly better suited as a long-term test system, e.g. in pharmacology, than the current short-lived in vitro cultures.

Due to the fast generation of aggregates, this test system can be used as a high-throughput test system which hitherto does not exist on the market based on the level of unions of cells.

In this context, an important factor is the preparation time. Thus, the protocol could be improved in the course of the studies insofar as 6 larvae can be prepared within a quarter of an hour and a 6-well plate can thus be prepared within this period of time. As there is a possibility to generate three up to a maximum of 5 heart cell aggregates in passage 0 from one larva, the highest number which can be assumed is 30 cardiomyocyte aggregates. In the best of cases, a 96-well plate can be inoculated by the preparation of 20 fish larvae within a working time of 50 minutes.

The cell cultures prepared according to the invention which, besides the cardiomyocytes and other heart cells, also contain further cell types, can further also be employed for testing the effect of non-heart-specific biological active substances, including cosmetics and pharmaceuticals, on these cell types in an advantageous manner.

All these tests can be performed with any candidate substances of interest according to standard methods and the conditions can be optimized by the person skilled in the art with ease using routine tests.

The following non-limiting examples and figures will explain the present invention in more detail.

DESCRIPTION OF THE FIGURES

The patent or application file contains at least one drawing executed in color. Copies of this patent or patent application publication with color drawing(s) will be provided by the Office upon request and payment of the necessary fee.

EXAMPLE 1

Preparation and Characterization of the Cell Aggregates

Animals used: Rainbow trouts (*Oncorhynchus mykiss*, Walbaum) in different development stages from eggs in the eyed egg stage to larvae at the end of the yolk sac stage were used for the experiments.

Preparations:
1: Eggs from a rainbow trout were incubated in a 0.01% formaldehyde solution for 15 minutes and were subsequently washed twice with PBS (Dulbecco's Phosphate Buffered Saline, Gibco Invitrogen, Paisley, UK). The embryo was subsequently isolated from its egg using scissors and forceps.
2: Larvae were anesthetized with tricaine methanesulfonate (MS-222) (0.05 mg/ml of aquarium water). DMEM/20% FBS medium:

To DMEM (Dulbecco's Modified Eagle Medium) with 4.5 g/l of glucose (Gibco, Karlsruhe) 1% penicillin (10,000 units/ml)/streptomycin (10 mg/ml) (PAA Laboratories, Austria) and 20% fetal bovine serum (PAA Laboratories, Paschin, Austria) were added.

The embryos or larvae were in each case incubated in 500 µl of 0.1% trypsin/EDTA, dissolved in PBS (PAA Laboratories, Austria), for 30 seconds to 2 minutes and at the same time additionally mechanically comminuted using scissors. The enzymatic digestion was stopped by transferring the tissue into 5 ml of the DMEM/20% FBS medium using a 1000 µl pipette (Sarstedt, Germany). Everything was subsequently centrifuged at an RCF of 130 for 5 minutes. The formed pellet was resuspended in 2.5 ml of medium and the cell suspension of each larva was placed into a 6-well plate (Techno Plastic Products AG (TPP), Trasadingen, Switzerland). The cells were kept at 20° C. and 1.9% $CO_2$. After two days, the medium was changed for the first time, the existing medium and all the non-adhered tissue pieces and cells being removed as well and the same amount of fresh medium being added. If any contaminations by bacteria or fungi are present, gentamycin (10 mg/ml; Biochrom AG, Germany) and kanamycin (5 mg/ml; Biochrom AG, Germany) as antibiotics and amphotericin (250 µg/ml; Biochrom AG) as an antimycotic were added.

Results:

Formation of Beating Cell Aggregates

Beating cell aggregates could typically be detected in the cell culture of the prepared rainbow trout larvae 7 days after the preparation by means of a microscope (Axiovert 40C; Zeiss, Germany) and video recordings. In rare cases, these already formed after three days. The morphologies of these aggregates were in part very different. They were typically spherical in passage zero and were beating very regularly. In contrast, they showed a tubular structure in passage 1 and also twitched in a very uncontrolled manner and at several sites in the same tissue. Passage 1 was achieved by trypsinization of the cell cultures. To this end, the medium of the culture was extracted by suction and the cells were rinsed with PBS. Detachment of the cells were subsequently achieved by an incubation with 0.1% trypsin/EDTA for 1 min at 37° C. By adding three times the volume in medium, the digestion was stopped and the cells were centrifuged at an RCF of 130 for 5 min. The tubular, twitching aggregates appeared in the cultures from day 10 after the passaging, while it was not necessary that a beating aggregate was already present in passage zero.

Probability of the Formation of Beating Aggregates

Figure 1:
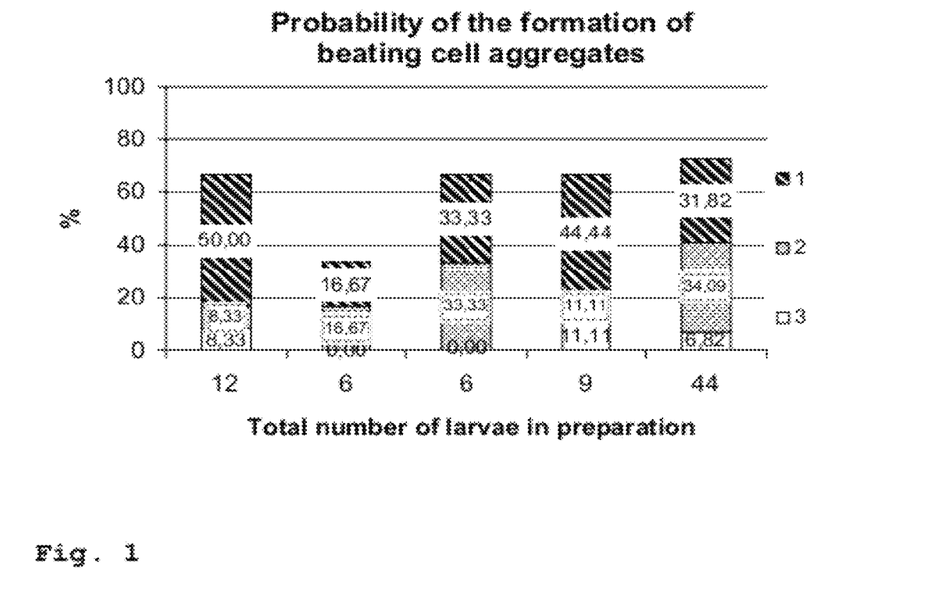
FIG. 1 Percentage of preparations in which 1 (white), 2 (dark gray) or 3 (light gray) spontaneously beating cell aggregates were formed in passage zero. Each column shows a preparation day with the number of prepared larvae.

To calculate the probability of the formation of beating aggregates, the number of prepared larvae with fully formed beating aggregates was divided by the total number of prepared larvae. The preparations showed that spontaneously rhythmic beating cell aggregates could be formed with a probability of more than 70%. Up to three spontaneously contracting cell aggregates could be formed from the preparation of a single larva (FIG. 1).

Beating Frequency

Figure 2:
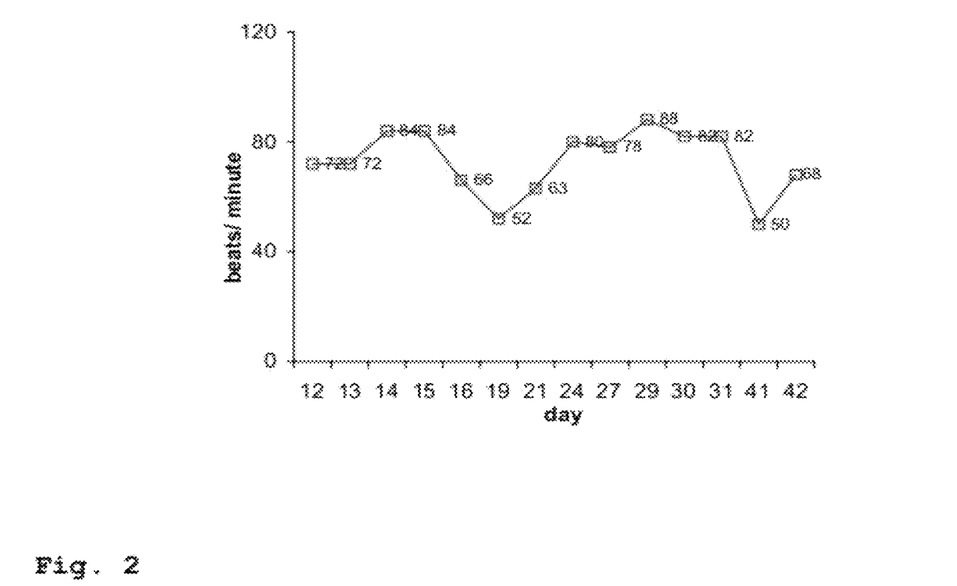
FIG. 2 Beating frequency of a cell aggregate in passage zero. Measurement by video recordings under a microscope (Axiovert 40C; Zeiss, Germany) and subsequent optical counting.

Furthermore, it could be shown that the aggregates displayed a contraction for a longer period in time, the cell aggregates beating steadily during the measurement by microscope (Axiovert 40C; Zeiss, Germany) and video recordings. The beating frequency per minute of a spontaneously contracting cell aggregate from passage zero of a prepared rainbow trout larva over a period of time of 42 days is exemplarily depicted in FIG. 2. The deviations in the frequencies which in this case were between 50 and 88 beats per minute could have been caused by stress factors, such as, e.g., exhausted medium or long exposure under the microscope.

Propagation and Regeneration of the Cell Aggregates

Figure 3A:
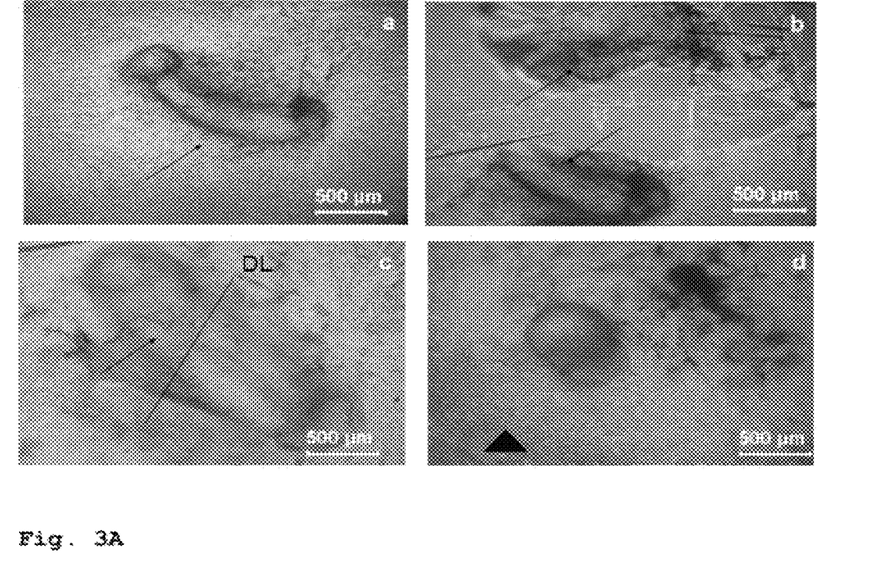
FIG. 3A Propagation of a beating cell aggregate in passage 1 by mechanical division. (a) Aggregate before the division (the arrow indicates the cutting site) and (b) both parts immediately after the separation (arrows). (c and d) Contracting elements reorganized after 7 days and remarkably additional contracting elements are formed de novo (arrow). DL ("Dividing Line") designates the site at which the parts were originally separated from each other. Cells from the cell aggregates also grew into monolayers (arrow head).

The propagation of an aggregate from passage 1 is depicted in FIG. 3A. It could be shown by mechanical division of individual aggregates by means of a scalpel and subsequent transfer of both parts into individual fresh wells that the aggregates can be propagated. After a regeneration period of several days, both parts began to beat again. Despite the separation of the aggregates, both portions are thus still able to contract. The isolated region can also be regenerated such that the original form is achieved again and the new region also displays a contraction. Therefore, multiple propagation of an aggregate cannot be excluded. The phenomenon suggests several heart pacemaker cells and/or the generation of heart pacemaker cells.

Figure 3B:
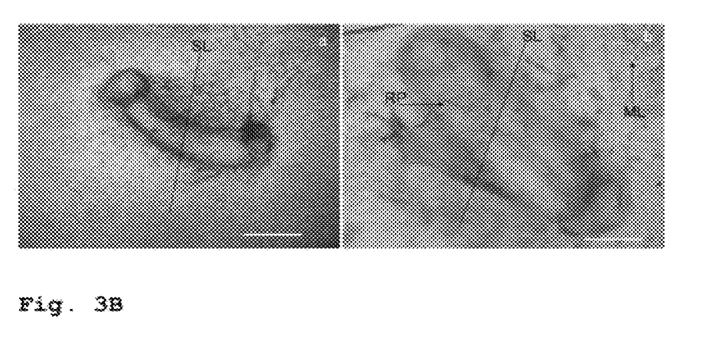
FIG. 3B Regeneration of a cell aggregate

FIG. 3B shows that the other region was newly formed after the separation.

Figure 11:
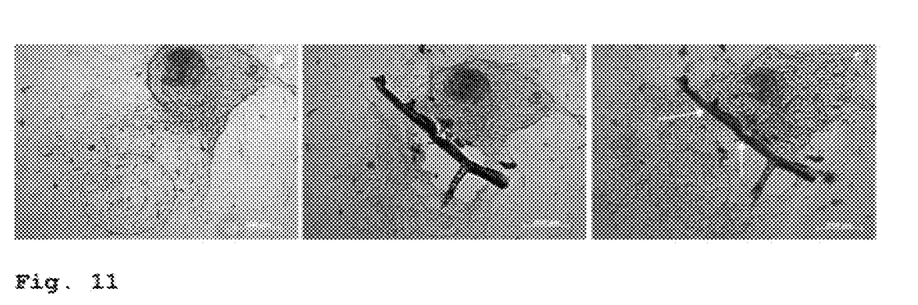
FIG. 11 Regeneration of cell aggregates in passage 0; a: before lesion; b: immediately after lesion; c: 2 weeks after lesion; arrows indicate regenerated cells FIG. 12 A: cell proliferation of divided/lesioned aggregates; B: (a) control; (b): divided aggregate FIG. 13 Longitudinal section of a heart cell aggregate (EM)

The coalescence of cells is possible within an aggregate after the separation. FIG. 11 proves that the contraction is beginning again despite a lesion (red circles) and adjusts itself to the original frequency (before the lesion). FIG. 11 a: before lesion; b: immediately after lesion: c: 2 weeks after lesion; arrows indicate regenerated cells.

Figure 12A:
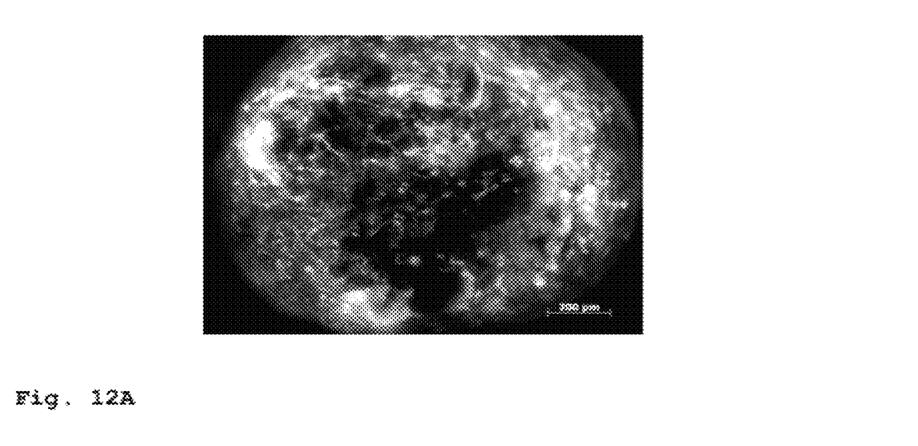
Figure 12B:
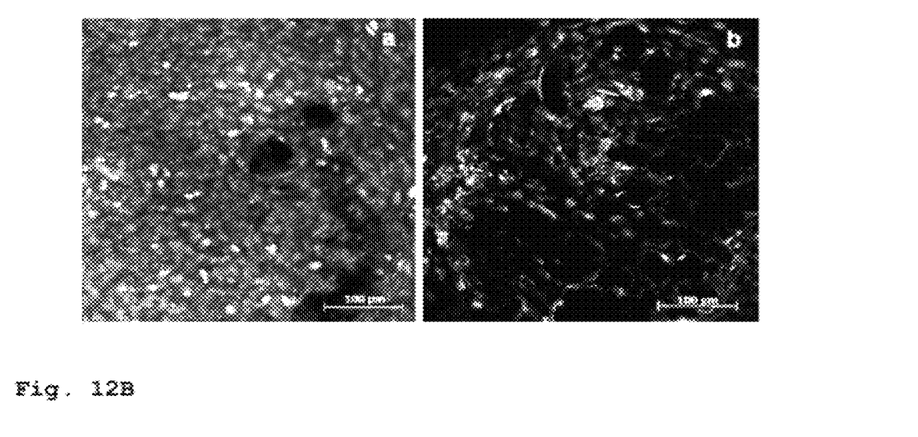

To detect the cell division of cardiomyocytes during the regeneration of the aggregates, the proliferation analysis was tested by including EdU (green). The aggregate was lesioned by piercing the middle of the aggregate. This can be clearly seen in FIG. 12 in the immunostaining as a black region in the middle. The troponin I structures (red) can be clearly seen as the proof for heart cells around the lesion. EdU-positive cells which prove actively proliferating cells can be found directly at the edge of the aggregate and going into this. The cell nuclei which were not divided are blue.

A undivided aggregate was additionally stained as the control. Images of both stainings were made in one plane and a z stack by means of LSM. The results showed (FIG. 12B) that the undivided aggregate has less EdU-positive cells (green) and that these also are randomly distributed throughout the entire aggregate. In contrast, the divided aggregate (b) displayed greater appearance of EdU-positive cells in the region of the lesion such that a high cell proliferation can be assumed in this case.

Examination of the Reaction of Cell Aggregates on the Addition of Potassium

The reaction of a cell aggregate which had already contracted for 16 days in culture on potassium could be tested in another experiment. It was shown under a light microscope (Axiovert 40C; Zeiss, Germany) with video recordings that the beating frequency of this aggregate increased from 66 beats per minute to 72 beats per minute over a period of 10 minutes. After these 10 minutes, a 1.75 mM potassium chloride solution was added. After adding the KCl solution, the contraction of this aggregate was beating with triple the speed as before for 6 seconds and then slowed down until it stopped 10 seconds after the addition and no more contractions could be observed. After removing the medium containing the 1.75 mM KCl solution and replacing it with fresh DMEM/20% FBS, the cell aggregate began to beat again after 2 minutes. However, the beating frequency was at first only 16 beats per minute which recovered to the original frequency within the next three days.

EXAMPLE 2

Identification of Cardiomyocytes

1. Detection of Heart-Specific Proteins by Means of Immunocytochemistry and Immunohistochemistry:

The detection by the antibodies used was initially tested on specificity on rainbow trouts. It was thus shown that the following antibodies in the case of rainbow trouts are only directed against those heart proteins as also occur in humans and mice.

Preparation for Immunohistochemistry

The heart of an adult rainbow trout was frozen for 30 seconds in isopentane and subsequently for one minute in liquid nitrogen. The organ was cut into 12 µm thick tissue pieces using a cryostat. The tissue sections are applied to physically or chemically activated cover slips and covalently attached to the glass surface. The cover slips with the applied tissue sections are divided into millimeter-sized fragments (BioChips™, Euroimmun, Lübeck, Germany) and applied to test fields of slides (BioChip Mosaics™, Euroimmun, Lübeck, Germany).

Preparation for Immunocytochemistry

One day before immunostaining, the cell aggregates were transferred onto Chamber Slides (BD, Bioscience, Bredford, Mass., USA) by carefully cutting them out of the original well using a scalpel and detaching them. The aggregate was transferred by carefully collecting it with a pipette. The aggregate was further cultivated over night at 20° C. and 1.9% CO2 in DMEM/20% FBS.

The preparations for the immunostaining of the aggregates included removing the old medium and rinsing twice with PBS. Fixation was carried out with 1 ml of methanol:acetone (7:3, −20° C.) and 1 µl of DAPI (4',6-diamidino-2-phenylindole, Roche, Basel, Switzerland) per well. After incubation for five minutes and nucleus staining at room temperature, rinsing with PBS was carried out three times.

For the preparations for immunohistochemistry and immunocytochemistry, the non-specific bonds were blocked by 16.5 µl of goat normal serum (Vector Laboratories, Burlingame, Calif., USA), dissolved in 1 ml of PBS, for 20 minutes at room temperature.

Figure 4:
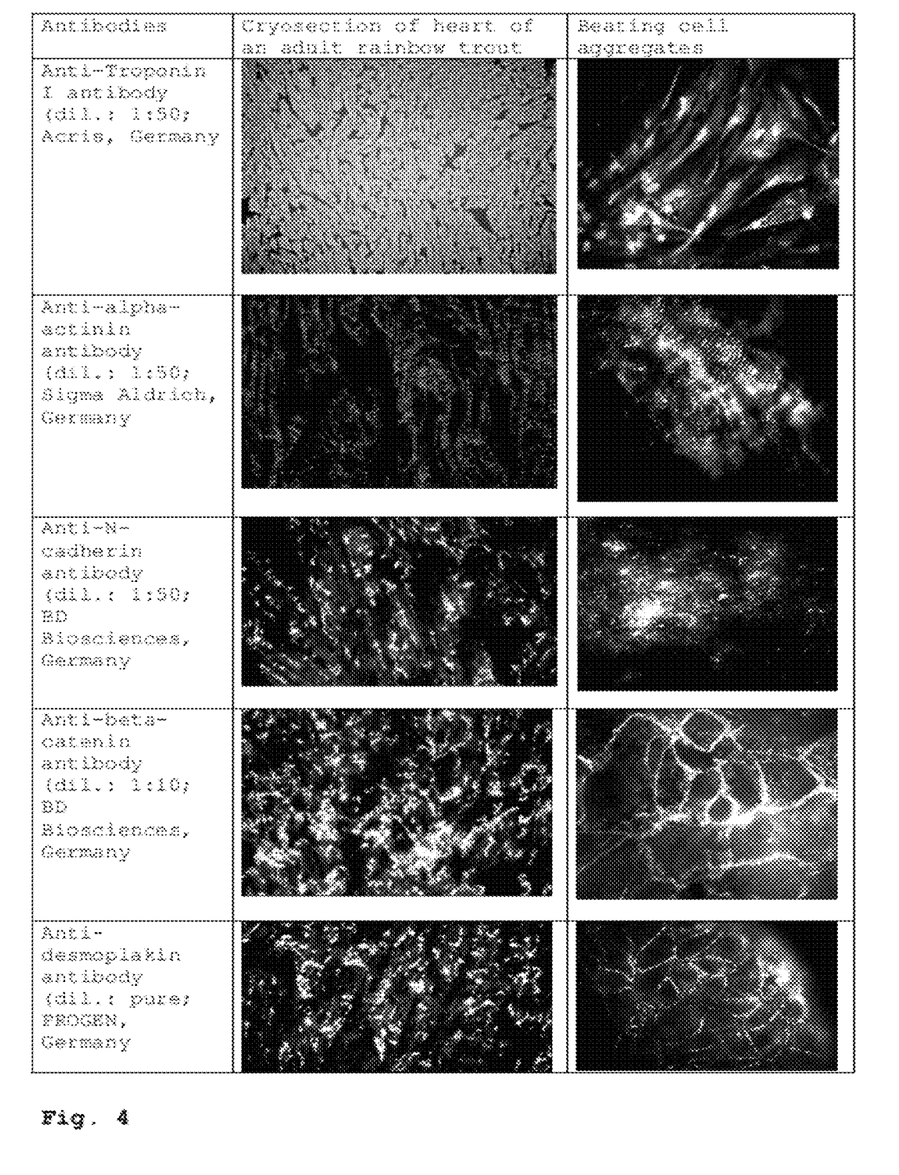
FIG. 4 Immunochemical analysis with heart-specific antibodies. The middle column shows an immunohistochemical examination of cryotome sections from heart tissue of an adult rainbow trout. As a comparison, immunocytochemical examinations of the contracting cell aggregates were carried out.

After removing the blocking solution by suction, the specific primary antibody was added. The dilution of the primary antibodies was produced with TBST+0.1% BSA (see FIG. 4, column 1). The incubation in a humid chamber at 37° C. was carried out for one hour, followed by rinsing three times with PBS. Subsequently, the secondary antibody Cy3 (conjugated AffiniPure goat anti-mouse IgG (High+Low); dil.: 1:400 with PBS; Jackson Immunoresearch Laboratories Inc., USA) is applied which was also incubated in a humid chamber for one hour at 37° C. At the end of the staining, it was again rinsed three times with PBS and the preparation was subsequently conserved with a cover slip and Vectashield (Vector Laboratories, Burlingame, Calif., USA). The evaluation was carried out on an Axioskop 2 mot plus fluorescence microscope (Carl Zeiss Vision GmbH, Hamburg).

The immunostainings (FIG. 4) showed that the antibodies have bound to the proteins typical for the heart, also in the beating areas. The anti-troponin I antibody has bound against troponin I and anti-alpha actinin against the proteins in the Z band of the cardiomyocytes. Furthermore, it could be detected that the anti-N-cadherin and anti-beta-catenin antibodies which are markers for Fascia adhaerens and likewise the anti-desmoplakin antibody have bound against the respective specific proteins.

2. Electron Microscopy

A more precise detection of occurring cardiomyocytes could be provided by electron microscopy. Beating cell aggregates from prepared larvae from the eyed egg stage and larvae which had hatched 1-2 days before were used for the examination. Large areas of the beating aggregates which were 3 weeks old were cut with a scalpel and detached. The cell tissue was fixed in MONTI (2.5% glutaraldehyde in 0.1M cacodylate buffer) for 24 h and subsequently rinsed in PBS for one hour. Post-fixation was carried out with 1% $OsO_4$ in 0.1M cacodylate buffer for 2 hours. The samples were subsequently dehydrated with ethanol and embedded in Araldite (Fluka, Switzerland). Subsequently, ultra-thin sections were incubated in uranyl acetate and lead citrate (Ultrostainer Carlsberg System, LKB, Sweden). After completion, the evaluation was carried out on a Philips EM 400 electron microscope (Philips, The Netherlands) at 60 kV.

Figure 5:
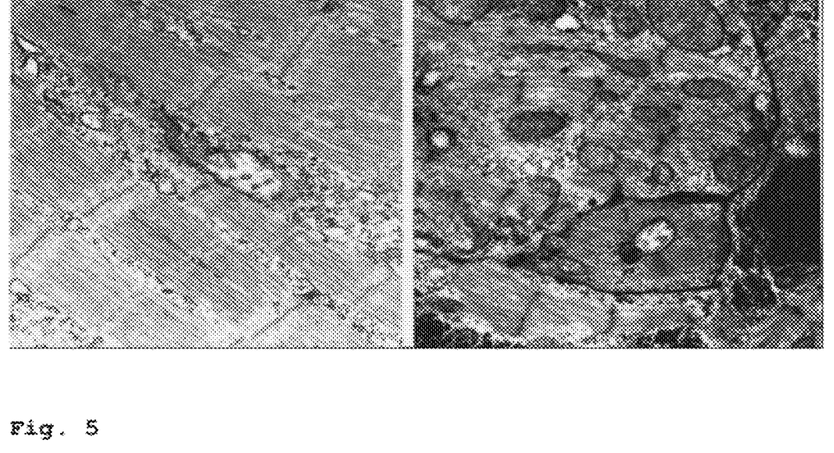
FIG. 5 Electron microscope images of a spontaneously contracting cell aggregate. (a) depicts a fully formed cardiomyocyte with the typically striped musculature with actin filaments and myosin filaments. (b) depicts a cell which is developing to become a heart cell. The beginnings of the striped musculature are notable.

The electron microscopy showed that the beating cell aggregates featured typically striped heart musculature with actin and myosin filaments (FIG. 5a). Furthermore, it became clear in the areas that, besides the already fully developed cardiomyocytes, cells which are still in the process of differentiation to heart cells are also present (FIG. 5b). As the differentiation often related to neighboring cells of already formed cardiomyocytes and the differentiation also took place with the first muscle filaments at the cell edge, this could be an indication of a cell-cell communication.

EXAMPLE 3

Detection of New Formation/Regeneration of the Heart Aggregates

Stereomicroscopic Observations

Figure 6:
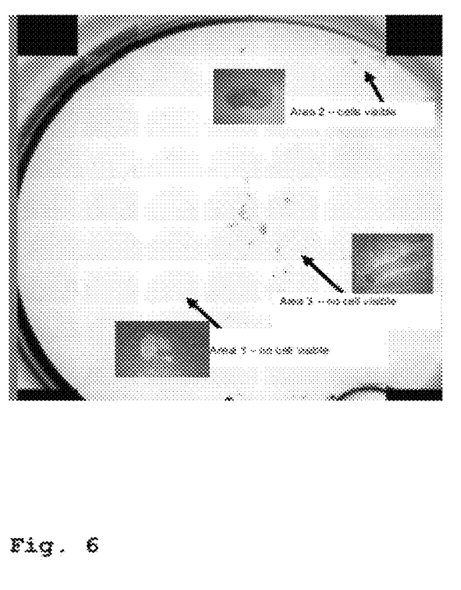
FIG. 6 Stereomicroscope images (Discovery. V8; Zeiss, Germany) of a rainbow trout cell culture. Formation of the area 1 7 days after preparation; area 2 already existed at the start and started to contract spontaneously on day 14. Area 3 was formed newly after three weeks in culture.

The experiment to detect the new formation or regeneration of the detected cardiomyocyte aggregates was carried out after the first medium change which took place two days after the preparation. An overview of the well in which the cells/tissue from the prepared larva had been cultivated was taken with the Discovery. V8 stereomicroscope (Zeiss, Germany) and the software Axiovision Rel 4.7. Another documentation was performed when a spontaneous contraction of a heart cell aggregate occurred. The cell cultures were in each case checked on contraction aggregates on Monday, Wednesday and Friday. An overview of a larval cell culture which formed three beating heart aggregates within three weeks is shown in FIG. 6. It could be determined that aggregate 1 which occurred after one week and aggregate 3 (beginning of contraction after three weeks) have formed anew. In contrast, aggregate 2 (beginning of contraction after 2 weeks) already existed in the first documentation.

EXAMPLE 4

Figure 7:
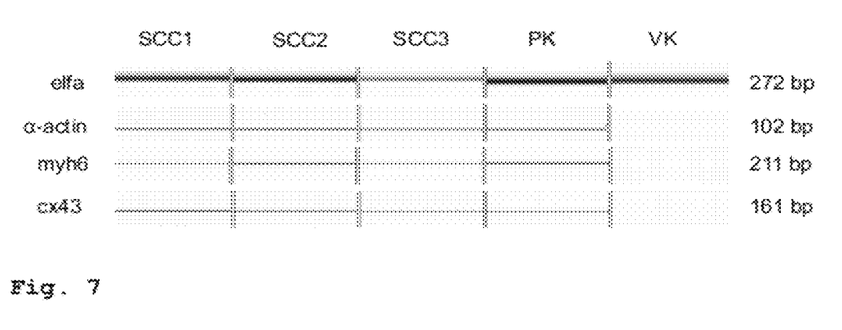
FIG. 7 PCR assay for detecting cell connection proteins in the cell aggregates

Characterization of the Cell Aggregates as a Functioning Syncytium/Union of Heart Cells Besides the already mentioned typical heart muscle markers (alpha-actin, actinin, myosin, troponin I), proof of cell connection proteins or gap junction/fascia adhaerens was also established. In this context, connexin 43, β-catenin, desmosomal structures and N-cadherin could be detected in the contracting cell aggregates by means of electron microscopy, PCR (FIG. 7) and immunochemistry. These cell connection structures which are evenly distributed throughout the entire aggregate show that the heart cell aggregate is a functioning syncytium. Thus, it can be considered as a self-contained and spontaneously functioning heart cell aggregate in which heart muscle cells are electrically coupled with other heart muscle cells. Furthermore, heart pacemaker cells exist in the aggregate due to the spontaneous and even contraction.

The syncytium is of particular importance for applications as it can be aimed for examinations on the level of unions of cells and not only on the level of individual cells. Thus, the cause-and-effect complexes can be examined more closely.
Explanation of FIG. 7:
PCR: elfa—housekeeping gene, a-actin—alpha-actin; myh6—cardiac myosin heavy chain 6; cx43—connexion 43. SCC1-SCC3—samples of heart cell aggregates, PK—positive control (heart of an adult rainbow trout); NK—negative control (non-cardiac cells from P3 of a rainbow trout larva)
Electron-Microscopic Images:
Besides the striped musculature and division into sarcomeres, the inclusion of intercalated discs representing the junctional complex is another indication of the formation of complex heart cell aggregates and not plain cardiomyocytes. This complex is responsible for the cell connection. Diverse gap junctions could be found in the aggregates. Furthermore, T-tubuli were also detected which, like in human cardiomyocytes, are on the level of Z-bands and are also mostly associated with a sarcoplasmic reticulum cistern. Heart muscle cells also possess a high number of mitochondria in cytoplasm to ensure the aerobic metabolism which is critical for the heart. Additionally, mitochondria could be detected in the generated aggregates via electron microscopy.

Figure 13:
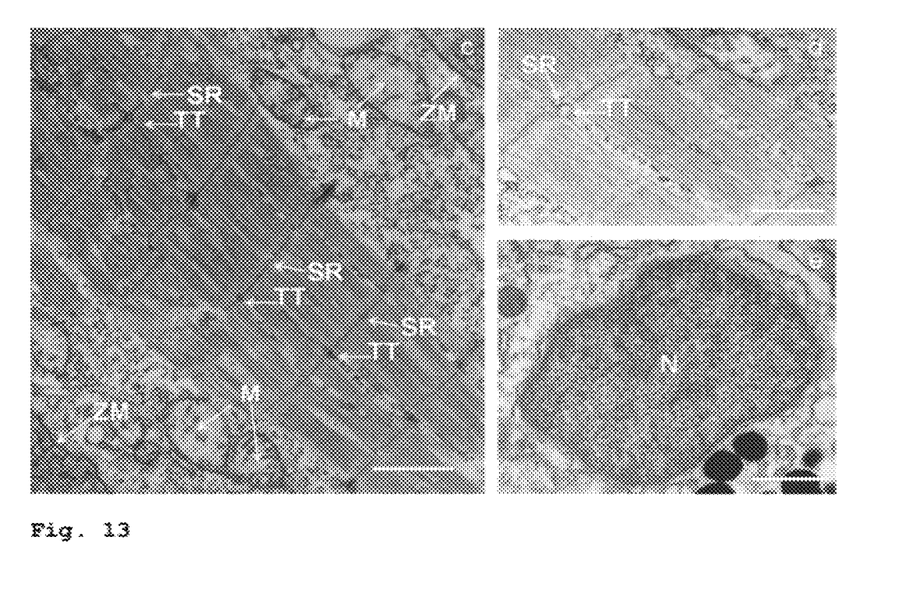

FIG. 13 depicts a longitudinal section through a heart cell aggregate (electron-microscopic image). The transversally oriented portions of the intercalated disc consist of fascia adhaerens and diverse desmosomes (detected by means of immunofluorescence) (a, b). Sarcomeres with sarcoplasmic reticulum (SR) and T-tubule (TT) in the Z-slices as well as mitochondria (M). Sarcoplasmic reticulum (SR) combined with T-tubule (TT) (d). Detection of nuclei (N) (e). Scale: 1 μm.

The generated aggregates are also of great interest for applications in developmental biology as processes can be examined on a cell level here. In this context, proof was established by means of EM that the cardiomyocytes form through cell-cell communication. Images of incompletely formed cardiomyocytes showed only sporadic muscle filaments at the cell edge which made it look like the beginning of a differentiation to cardiomyocytes. Furthermore, the beginning of transverse striations were also seen in the neighboring cells of these cells, the striations also being located at the cell edge to the neighboring cells. In these cases, the impression of a cell-cell communication for the generation to heart cells is given.

Figure 14:
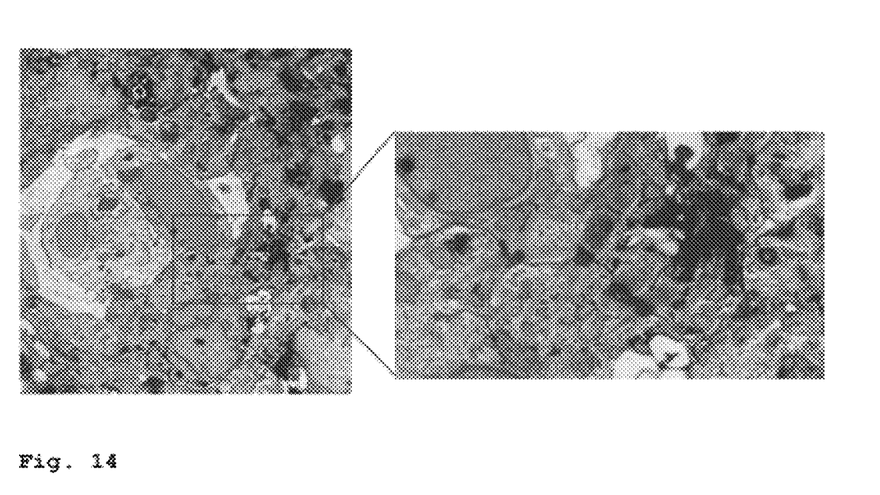
FIG. 14 Formation of a heart cell (EM)

FIG. 14 depicts the formation of a heart cell. First sarcomeres can be seen at neighboring cells.

EXAMPLE 5

Electrophysiology of the Cell Aggregates

The electrophysiology is important for the use of the cell aggregates as a test system in pharmacology. Measurement of the electric activity was performed by means of extracellular measurement via MEA (multi-electrode array) and intracellular measurement via a sharp electrode.

3.1. Extracellular Derivation

The extracellular signal derivation of cardiac cells by means of a multi-electrode array (MEA) allows for the simultaneous detection of the activity at several points of a cell network.

The examinations with the MEA proved that the cells of the aggregate work together as it is also the case in the heart of all vertebrates, and that action potentials can be measured in the entire aggregate. The transmission property confirms the detection of a functioning union of cells.

Figure 8A:
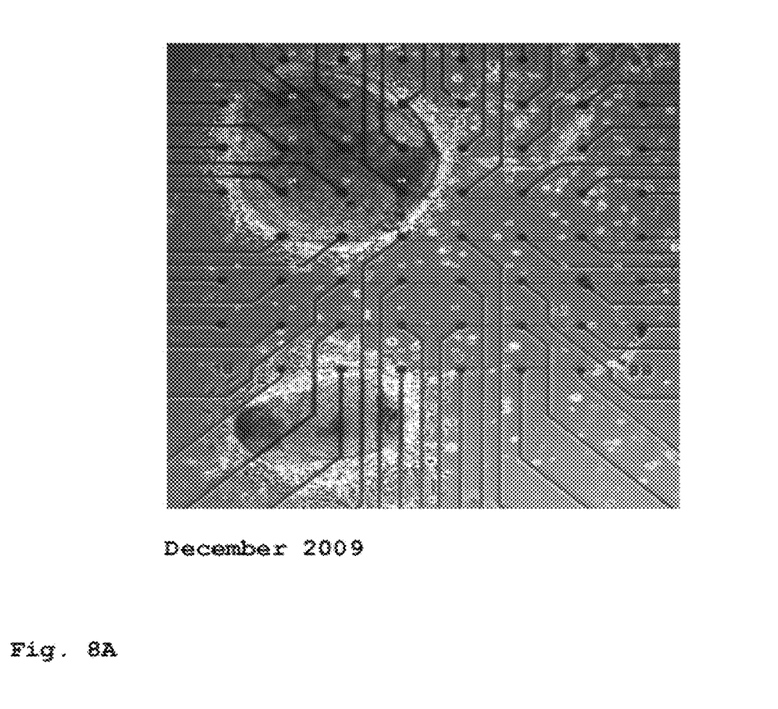
FIG. 8 Growth and coalescence of cell aggregates on an MEA
Figure 8B:
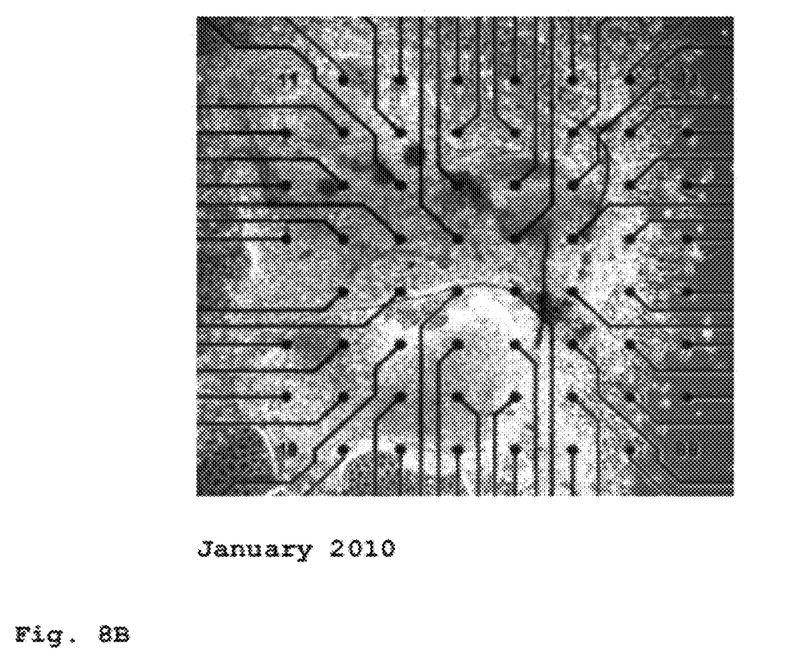

It can be seen from FIG. 8 that the aggregates grow by cell propagation, on the one hand, such that they occupy more electrodes and enlarge their field potential. Furthermore, they also change their position on the MEA. The small aggregate which was lower in FIG. 8 migrated towards the higher and bigger aggregate. At the end, both aggregates from two different larvae have coalesced (FIG. 8B) such that a contracting aggregate formed from originally two different contraction frequencies. Cell connection proteins are required for this which were formed in this case.

This specific characteristic that two cells from different organisms coalesce is a requirement in transplantation medicine. Thus, the phenomena of rejection could be investigated better with these heart cell aggregates.

3.2. Intracellular Derivation

In contrast to the extracellular derivation, transmembrane voltages can be measured by means of intracellular derivations. Through this, the mechanisms of potential generation, the membrane potential and the ion currents involved can be measured directly.

The properties of action potentials and the examination on certain channels (potassium and calcium channels) were carried out with a sharp electrode.

Figure 9:
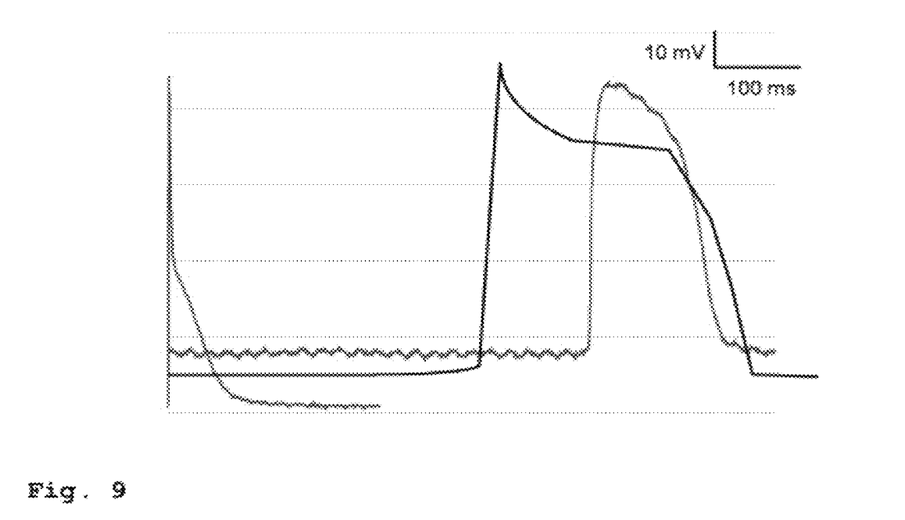
FIG. 9 Action potential parameters of the cell aggregates in comparison to mouse and human (intracellular derivation)

It could be proven that the action potential parameters of the aggregates are very similar to those of humans. A particular characteristic of human cardiomyocytes is the pronounced plateau phase which is also displayed by the generated aggregate (FIG. 9). In contrast, it is also demonstrated that mouse cells which are hitherto primarily used as test models differ strongly from human APs in terms of their electrophysiological potential and thus are unsuitable. Examinations of the aggregates also disclosed the correlation between the action potential duration and the period in time which also exists in higher (humans), but not in lower mammals (e.g. mice).

3.3. Drug Tests

The reaction of the aggregates on drugs which influence certain channels in the heart is of importance for the functionality as a test model. It was shown that the aggregates react on known cardiac drugs in the same manner as the human heart. Examinations were carried out with isoproterenol (calcium channel agonist) (FIG. 10A) and rilmakalim (potassium channel blocker). It could be observed that the aggregates recover after the drug testing by means of a medium change and are available for new experiments.

The invention claimed is:

1. An in vitro method for producing contracting fish cell aggregates, comprising the following steps:
   a) mechanical comminution and/or partial enzymatic digestion of fish embryos or fish larvae;
   b) transfer of the comminuted and/or partially digested fish tissue into an enzyme-free medium and removing the supernatant by centrifuging to obtain a cell pellet;
   c) resuspension of the cell pellet in a cell culture medium; and
   d) cultivation of cells in the cell culture medium, with the cell culture medium being changed at least once, until spontaneously contracting cell aggregates form.

2. The method according to claim 1, wherein the enzymatic digestion comprises a trypsin treatment.

3. The method according to claim 2, wherein the trypsin treatment is performed in a buffer with 0.01-1% trypsin for a period of 30 seconds to 2 minutes.

4. The method according to claim 1, wherein the cultivation of the cells in step d) is carried out for a period of at least 3 to 7 days.

5. The method according to claim 1, wherein the cell culture is passaged several times.

6. The method according to claim 1, wherein the cultivation is carried out at a temperature of 4-28° C. and a $CO_2$ content of 1-5%.

7. The method according to claim 1, wherein the fish embryos or fish larvae are selected from the species of Teleostei.

8. The method according to claim 7, wherein the fish embryos or fish larvae are selected from the group consisting of herrings (Clupeoidei), salmon-like fish (Salmonoidei), carps (Cyprinidae), eels (Anguillidae), perches (Percidae), cods (Gadidae), catfish (Siluroidae), flatfish (Pleuronectiformes), garfish (Beloniformes) and sturgeons (Acipenseriformes).

9. The method according to claim 8, wherein the fish embryos or fish larvae are selected from the species of salmon-like fish (Salmonoidei).

10. The method according to claim 9, wherein the fish embryos or fish larvae are derived from salmons, trouts, samlets, huchens, whitefish, graylings or smelts.

11. The method according to claim 1, wherein in step a), fish larvae are used 1-50 degree days after the hatching.

\* \* \* \* \*